(12) United States Patent
Wagener et al.

(10) Patent No.: US 7,754,842 B2
(45) Date of Patent: Jul. 13, 2010

(54) ELASTOMERIC POLYMERS

(75) Inventors: Kenneth B. Wagener, Gainesville, FL (US); John C. Sworen, Gainesville, FL (US); Hector F. Zuluaga, Cali (CO); Piotr Matloka, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 206 days.

(21) Appl. No.: 12/176,831

(22) Filed: Jul. 21, 2008

(65) Prior Publication Data

US 2008/0281068 A1 Nov. 13, 2008

Related U.S. Application Data

(62) Division of application No. 10/718,764, filed on Nov. 21, 2003, now Pat. No. 7,420,025.

(60) Provisional application No. 60/427,995, filed on Nov. 21, 2002.

(51) Int. Cl.
C08G 77/60 (2006.01)
(52) U.S. Cl. .......................................... 528/35; 528/33
(58) Field of Classification Search .................. 528/33, 528/35
See application file for complete search history.

(56) References Cited

U.S. PATENT DOCUMENTS 4,220,600 A    9/1980  Yajima et al.
4,358,576 A   11/1982  Yajima et al.
6,184,407 B1   2/2001  Yoshitake et al.
6,224,946 B1   5/2001  Kirchmeyer et al.
6,384,172 B1   5/2002  Dvornic et al.
6,613,834 B2   9/2003  Nakata et al.

OTHER PUBLICATIONS

Brzezinska et al., "Carbosilane/Carbosiloxane-Based ADMET Homopolymers and Copolymers Possessing Latent Reactivity," Journal of Polymer Science, Part A: Polymer Chemistry, vol. 38, 1544-1550 (2000).

*Primary Examiner*—Kuo-Liang Peng
(74) *Attorney, Agent, or Firm*—Saliwanchik, Lloyd & Saliwanchik (57) ABSTRACT

Acyclic diene metathesis (ADMET) has been utilized in the synthesis of carbosilane and carbosiloxane polymers bearing a latent reactive methoxy-functional group on each repeat unit. The polymerization results in a linear thermoplastic polymer. The latent reactive methoxy groups remain inert during polymerization; however, exposure to moisture triggers hydrolysis and the formation of a chemically cross-linked thermoset. The thermoset's properties can be modified by varying the ratio of carbosilane and carbosiloxane repeat units in the final material. Also, increasing cross-link density by using cross-linkable chain-end groups and increasing the run length of the soft phase, maximizing phase separation and elasticity, allows for the synthesis of elastic thermosets exhibiting good tensile strength. Adding a trifunctional ADMET active chain-end cross-linker to the system improved the mechanical behavior of the resulting polymer.

2 Claims, 3 Drawing Sheets

ELASTOMERIC POLYMERS

CROSS REFERENCE TO RELATED APPLICATIONS

This application is a divisional of U.S. patent application Ser. No. 10/718,764 filed Nov. 21, 2003, which claims priority of U.S. provisional patent application No. 60/427,995 filed Nov. 21, 2002, the entirety of which is incorporated herein by reference.

STATEMENT REGARDING FEDERALLY SPONSORED RESEARCH OR DEVELOPMENT

This invention was made with U.S. government support under grant number DAAD19-00-1-0160 awarded by the Army Research Office. The U.S. government may have has certain rights in the invention.

FIELD OF THE INVENTION

The invention relates to the fields of materials science and polymer chemistry. More particularly, the invention relates to elastic silicon-containing polymers and methods for synthesizing such polymers using acyclic diene metathesis (AD-MET) polymerization.

BACKGROUND

Silicon-based polymers have been known and used for several decades. Prominent among these are polymers based on polydimethylsiloxane (PDMS), commonly called silicones. PDMS-based polymers are useful in many different applications based on their low glass transition and high thermal stability. Such polymers, however, exhibit relatively weak mechanical properties. A number of techniques have been employed in an effort to improve the mechanical performance of these polymers. For example, adding silica-based fillers within the polymer matrix has been shown to enhance the overall mechanical properties of the material. As another example, carbon segments have been added to the PDMS-based polymers to create silicon/carbon copolymers. These silicon/carbon-based copolymers display several desirable material properties not observed in polymers based on carbon or silicon alone. Such properties include high thermal stability, good electrical resistance, low surface tension, good release and lubrication properties, high hydrophobicity, low glass transition, and low toxicity for the natural environment.

Although much progress has been made in this field, the need for new carbon/silicon polymers that exhibit improved physical properties remains. In particular, new carbon/silicon polymers that exhibit both high elasticity and good tensile strength would be useful in many different applications.

SUMMARY

The invention relates to the development and characterization of internal and chain-end cross-linked carbosilane/carbosiloxane copolymers and silicon/carbon hybrid tripolymers. In particular, ADMET was utilized to synthesize carbosilane and carbosiloxane polymers bearing a latent reactive functional group on each repeat unit. The polymerization resulted in a linear thermoplastic polymer. Although, the latent reactive groups remained inert during polymerization, exposure to moisture triggered hydrolysis and the formation of a chemically cross-linked thermoset.

The thermoset's properties can be modified by varying the ratio of carbosilane and carbosiloxane repeat units in the final material. Increasing cross-link density using cross-linkable chain-end groups and increasing the run length of the soft phase to maximize phase separation and elasticity, allowed for the synthesis of thermosets of high elasticity and good tensile strength. Introducing a trifunctional ADMET active chain-end cross-linker to the carbosilane/carbosiloxane reaction mixture resulted in a film that exhibited enhanced elasticity. Changing the soft phase monomer from a siloxane to a polyoxyethylene glycol further enhanced material properties. For example, a cross-linked film containing chain-end cross-links, chain-internal cross-links, and the diundecenyl triethylene glycol in a soft phase exhibited good material properties (modulus 6 MPa; elongation 500%).

Accordingly, the invention features a molecule including a polymer having the structure:

wherein A is a carbosilane including a latent reactive group bonded to Si, B is a carbosiloxane, x is an integer greater than or equal to 1, and y is an integer greater than or equal to 1. The latent reactive group can be, for example, a hydrogen, an alkoxy group (e.g., a methoxy group), a phenoxy group, or a halogen atom. The carbosilane can have the structure:

wherein R is a latent reactive group, $R_1$ is a hydrocarbon chain containing at least one carbon, and z is an integer greater than or equal to 1. The carbosiloxane can have the structure:

wherein R is any suitable group such as an alkyl (e.g., methyl), a phenyl, a hydrogen, or a halogen; and y is an integer greater than or equal to 1. As one example, the polymer can have the structure of compound 3 shown in FIG. 1.

The molecule of the invention can also include at least two polymers each having the structure:

wherein the at least two polymers are internally cross-linked via at least one Si—O—Si linkage. As one example, the molecule can include the structure of compound 4 shown in FIG. 1.

The molecule of the invention can also include a polymer having the structure:

wherein C is a chain-end cross-linking molecule and z is an integer greater than or equal to 1. The chain-end cross-linking molecule can be, e.g., compound 5 or 6 shown below; and the polymer can have the structure of compound 7 or 10 shown in FIGS. 2 and 3, respectively.

The molecule of the invention can also include at least two polymers each having the structure:

$$A_x\text{-}B_y\text{-}C_z$$

wherein the at least two polymers are internally cross-linked via at least one Si—O—Si linkage and chain-end cross-linked. For instance, the molecule can have the structure of compound 8 or 11 shown in FIGS. 2 and 3, respectively.

In another aspect, the invention features a method of making a polymer. The method includes the steps of: (a) preparing a reaction mixture including a carbosiloxane monomer, a carbosilane monomer, and an ADMET catalyst; and (b) placing the reaction mixture under conditions that result in the production of the polymer. The reaction mixture can include the carbosilane monomer and the carbosiloxane monomer in a molar ratio of about 100:1 to about 1:100 (e.g., 1:20). The molar ratio of the monomers to ADMET catalyst can be about 1:1 to about 5000:1 (e.g., about 250:1).

In variations of the method, the reaction mixture can further include a chain-end cross-linking molecule, and the molar ratio of the carbosilane monomer, the carbosiloxane monomer, and the chain-end cross-linking molecule can be about 1-100:1-100:1-100. In the method, the catalyst can be Grubb's second generation catalyst or Schrock's catalyst.

Step (b) of the method can include placing the reaction mixture under dry conditions, placing the reaction mixture in an argon atmosphere, subjecting the reaction mixture to a vacuum force, and/or adding heat to the reaction mixture. Performance of step (b) can result in the production of a non-cross-linked polymer which can be exposed to water (e.g., atmospheric moisture) to form a cross-linked polymer.

Unless otherwise defined, all technical terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions will control. The particular embodiments discussed below are illustrative only and not intended to be limiting.

DETAILED DESCRIPTION

The invention provides carbosilane/carbosiloxane copolymers and silicon/carbon hybrid tripolymers that can be internally and/or chain-end cross-linked. Also provided are methods for synthesizing these polymers. The methods are generally performed using ADMET to polymerize a carbosilane monomer having a latent reactive group, a carbosiloxane monomer, and optionally a chain-end cross-linking molecule. Cross-linking of the resulting linear polymers via the latent reactive group occurs upon exposure of the linear polymers to moisture. The resulting cross-linked polymers exhibit both good elasticity and high tensile strength.

The below described preferred embodiments illustrate adaptations of these compositions and methods. Nonetheless, from the description of these embodiments, other aspects of the invention can be made and/or practiced based on the description provided below.

General Methods

Various aspects of the invention utilize techniques known in the field of polymer chemistry. General polymer chemistry concepts and methods relating to the invention are described in Polymer Handbook (4th Edition), eds., Brandup et al., New York, John Wiley and Sons, 1999; and Polymer Synthesis and Characterization: A Laboratory Manual, eds. Sandler et al., Academic Press, 1998. Concepts and methods relating more specifically to metathesis chemistry are described in Alkene Metathesis in Organic Synthesis. Springer-Verlag: Berlin, 1998 and Olefin Metathesis and Metathesis Polymerization, 2d ed.; Academic: San Diego, 1997.

Polymers

Figure 1:
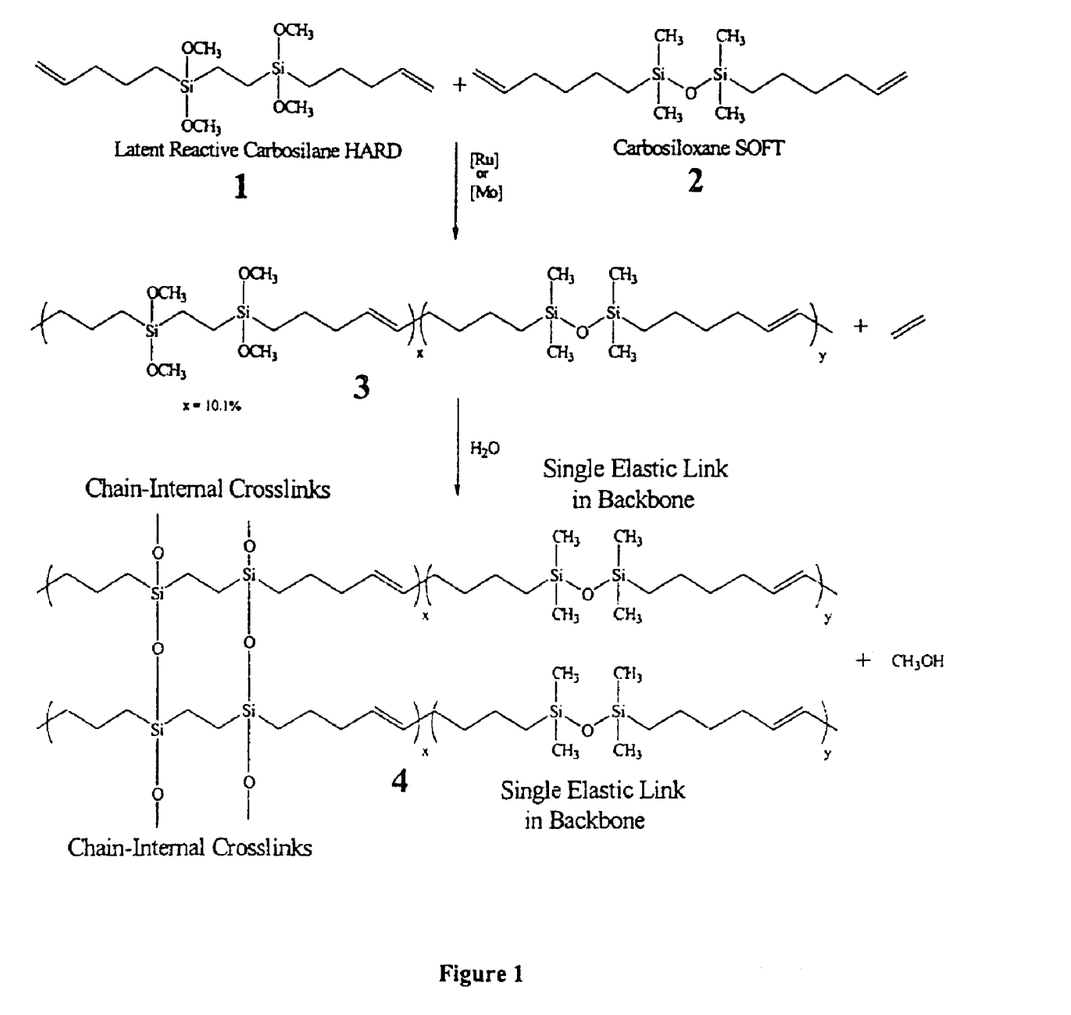
FIG. 1 is a highly schematic illustration of a method of making a carbosilane/carbosiloxane copolymer with and without internal cross-links from carbosilane and carbosiloxane monomers using ADMET.

The invention provides a variety of carbosilane/carbosiloxane-based polymers that can be internally or chain-end cross-linked. An exemplary polymer of the invention has the structure:

$$A_x\text{-}B_y$$

wherein A is a carbosilane including a latent reactive group bonded to Si, B is a carbosiloxane, x is an integer greater than or equal to 1, and y is an integer greater than or equal to 1. The latent reactive group can be, for example, a hydrogen, an alkoxy group (e.g., a methoxy group.), a phenoxy group, or a halogen atom. An example of one such polymer is listed in FIG. 1 as compound 3.

Figure 2:
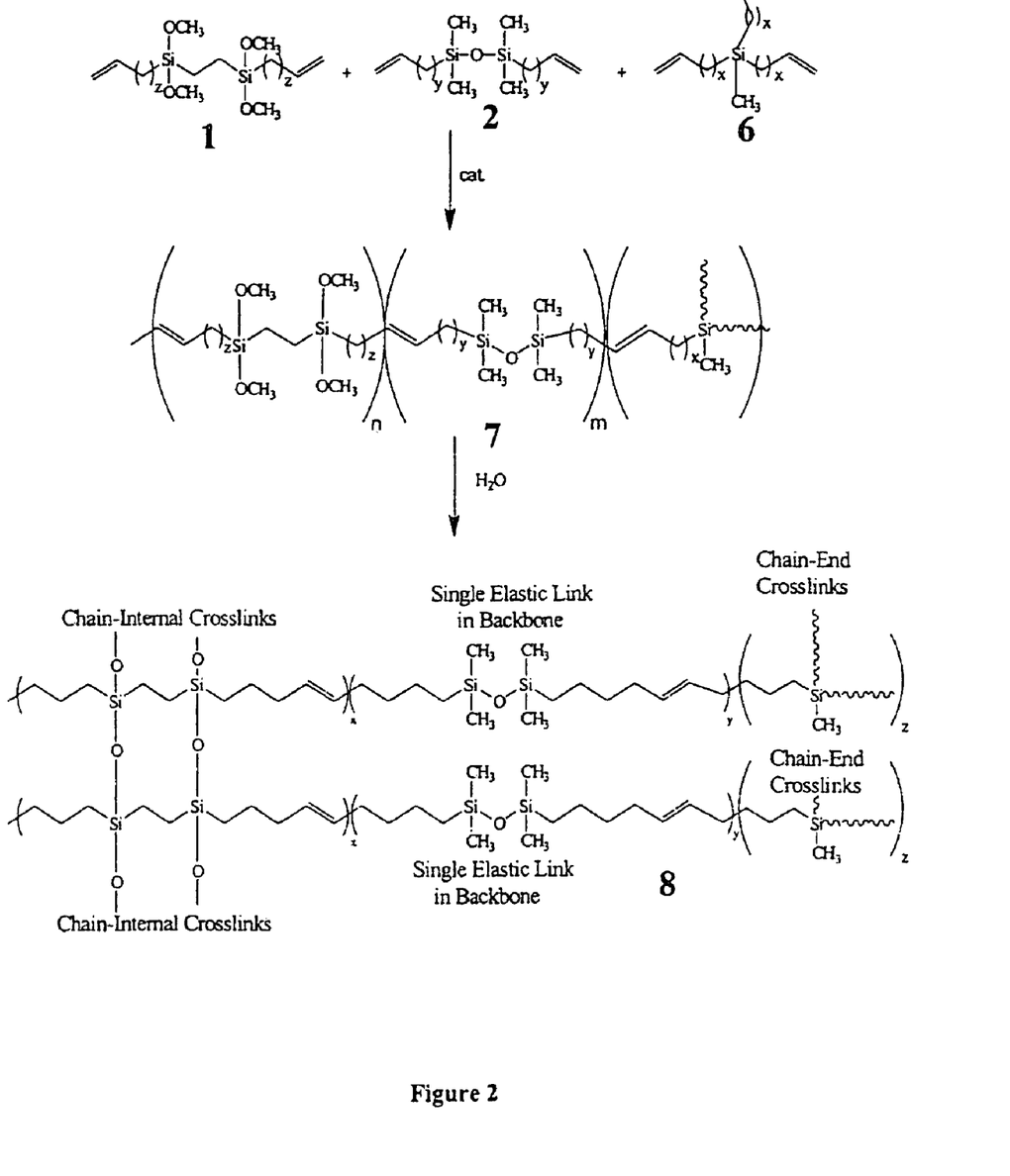
FIG. 2 is a highly schematic illustration of a method of making a carbosilane/carbosiloxane/chain-end cross-linker tripolymer with and without internal cross-links from carbosilane, carbosiloxane, and chain-end cross-linker monomers using ADMET.
Figure 3:
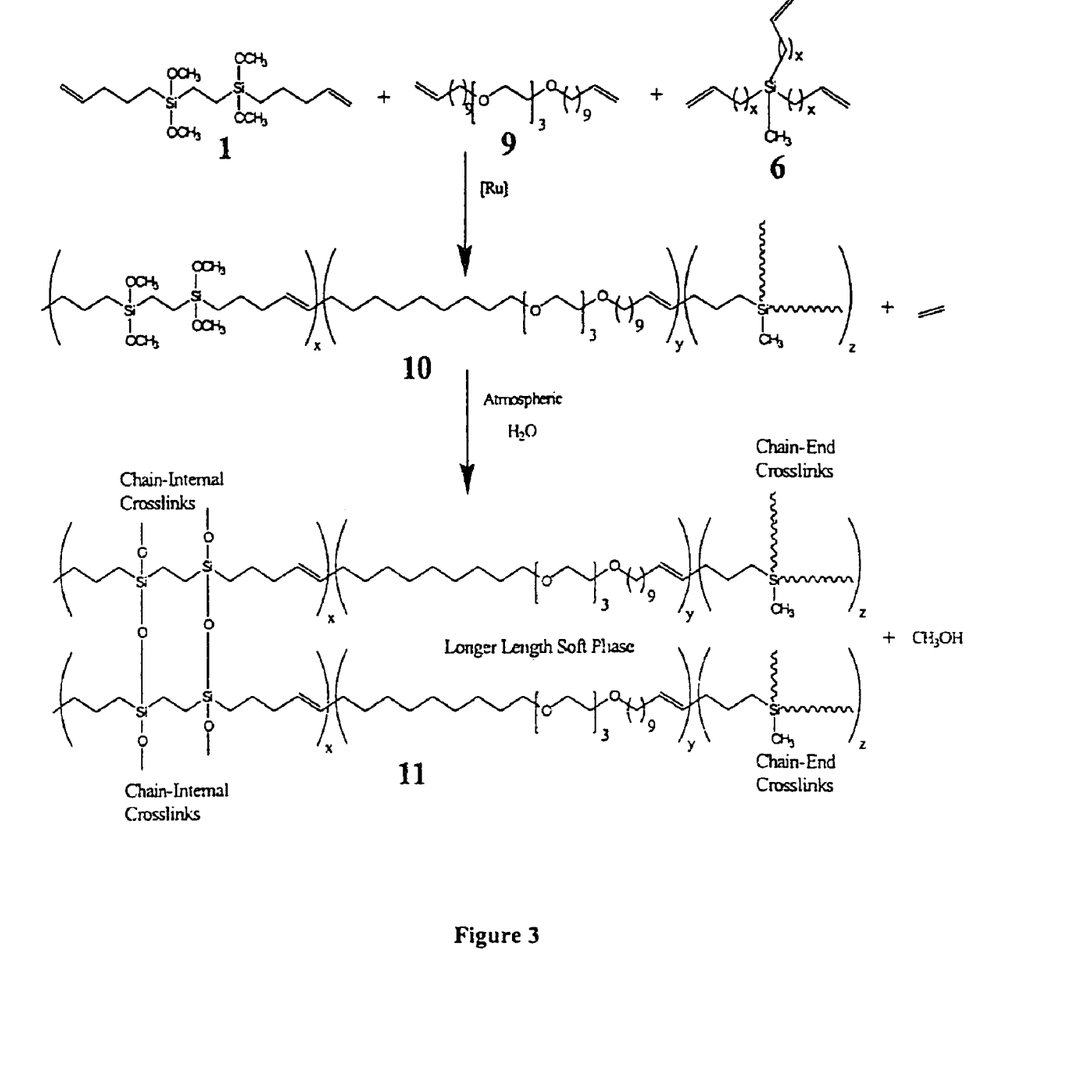
FIG. 3 is a highly schematic illustration of a method of making a carbosilane/carbosiloxane/chain-end cross-linker tripolymer with and without internal cross-links from carbosilane, carbosiloxane (longer length than in the reaction of FIG. 2), and chain-end cross-linker monomers using ADMET.

A related polymer of the invention additionally features a chain-end crosslinker and has the structure of:

$$A_x\text{-}B_y\text{-}C_z$$

wherein C is the chain-end cross-linking molecule and z is an integer greater than or equal to 1. Two examples of such a polymer are listed herein in FIGS. 2 and 3, respectively, as compounds 7 and 10.

The carbosilanes in the foregoing polymers contain latent reactive groups that, in the presence of water (e.g., atmospheric moisture), cause the polymers to form spontaneous internal cross-links via Si—O—Si bonds as illustrated in FIGS. 1-3. The polymers thus formed are also within the invention. Examples of such polymers are listed in FIGS. 1, 2, and 3, respectively, as compounds 4, 8, and 11.

The actual structure of the polymers of the invention is determined by the selection of the carbosilane, carbosiloxane, and any chain-end cross-linking molecules to be used as monomers. The structure of the carbosilane can be:

Generally, the length of the silane unit (Si—R$_1$—Si) can be as long as is desired, although the spacing between the Si and the double bond should be at least two CH$_2$ groups. R$_1$ can be, e.g., 2, 3, 4, 5, 6, 7, 8, 9, 10 or more carbons in length.

The latent reactive group (designated R) can be any functional group that is inert during ADMET but active upon introduction of a specific condition. In the examples described herein, for example, the latent functional group is methoxyl. This group remains stable during the ADMET reaction, but is thereafter readily hydrolyzable in the presence of moisture. Hydrolysis of this group results in the formation of internal cross-links (Si—O—Si bonds). In addition to methoxyl, the latent reactive group might take the form of a longer alkoxyl, H, a phenoxyl, or even a halogen such as Cl. The characteristics of the polymer will vary depending on the latent reactive group selected. In the reactions depicted in FIGS. 1-3, the use of methoxyl is preferred as it hydrolyzes relatively slowly during the cross-linking step and thereby allows shaping of the cross-linked polymer. In comparison, the use of Cl as the latent reactive group causes rapid hydrolysis and cross-linking; and the use of longer alkoxyls as the latent reactive group (e.g., ethoxy) causes slower hydrolysis and cross-linking.

The structure of the carbosiloxane can be:

The group designated R can be, e.g., H, a halogen atom such as Cl, an alkoxyl, or a phenoxyl. Generally, the length of the siloxane unit (Si—O—Si) can be as long is desired, although the spacing between the Si and the double bond should be at least two CH$_2$ groups.

The chain-end cross-linker can take the form of any molecule suitable for such use, e.g., a molecule having one or more (2, J, 4, 5, or more) terminal CH$_2$=CH$_2$'s: Examples of such molecules include those with the following structures:

n = min. 2
X = OMe, OR, NR2
R = (3-X) - any hydrocarbon

Examples of specific chain-end crosslinkers used in the examples described below include compounds 5 and 6 (x=an integer greater than or equal to 2) below:

Polymer Synthesis

A method for making a carbosilane/carbosiloxane polymer of the invention is performed by ADMET, a step-growth type of polycondensation, where the initial monomer molar ratios are directly transferred to the polymer produced. A carbosilane/carbosiloxane polymer of the invention is synthesized by first preparing a reaction mixture including a carbosiloxane monomer, a carbosilane monomer, an ADMET catalyst, and, optionally a chain-end crosslinking molecule; and then placing the reaction mixture under conditions that result in the production of the polymer. The reaction mixture can include the carbosilane monomer and the carbosiloxane monomer in any suitable molar ratio, e.g., 100:1 to 1:100. Where a chain-end cross-linker is used a molar ratio of carbosilane:carbosiloxane:chain-end cross-linker can also be any suitable molar ratio, e.g., 1-100:1-100:1-100. In general, for the synthesis of elastic polymers, a low carbosilane (and chain-end cross-linker) to carbosiloxane ratio should be used, while for the synthesis of more rigid polymers, a high carbosilane (and chain-end cross-linker) to carbosiloxane ratio should be used. In the reactions described below, polymers with good elasticity resulted when the reaction mixture included less than about 15% (molar) carbosilane and chain-end cross-linker).

The polymerization reaction is catalyzed using a carbene catalyst that is active in ADMET and is functional group tolerant. See, Louie and Grubbs, *Agnew. Chem. Int. Ed.* 2001, 40:247; and Trnka and Grubbs, *Acc. Chem. Res.,* 2001, 34:18; Bielawski et al., *Polymer,* 2001, 42:4939; international patent application WO 00/43343, and U.S. Pat. No. 6,048,993 In the exemplary methods described below, the catalyst used was Grubb's second generation catalyst or Schrock's catalyst:

Schrock's [Mo] catalyst

2nd generation Grubbs' [Ru] catalyst

The molar ratio of the monomers to ADMET catalyst can be about 1:1 to about 5000:1. For cost reasons, it is generally desirable to use the least amount catalyst sufficient to drive the reaction. Monomer:catalyst ratios of about 250:1 were used in the reactions described below. Typically, suitable monomer:catalyst ratios range from about 1200:1 to about 100:1.

After the reaction mixture is prepared it is placed under conditions that result in the production of the polymer. In general, the reaction mixture is placed under a dry, inert gas atmosphere (argon or nitrogen) at atmospheric pressure. The inert gas can be streamed over the mixture (e.g., when a hydrocarbon solvent is used in the reaction mixture). A vacuum may be applied (e.g., to reduce the pressure to less than about 1 mm Hg) to the reaction mixture to remove ethylene and drive the reaction forward. If Schrock's catalyst is used, the reaction can be carried out at room temperature. If Grubb's second generation catalyst is used, the reaction temperature can be higher, e.g., 65-70° C. The polymer that results from the foregoing steps lacks internal cross-links. Exposure of the polymer to water (e.g., atmospheric moisture) causes hydrolysis of the latent reactive groups and formation of internal cross-links (Si—O—Si bonds).

EXAMPLES

Example 1

Materials and Methods

General Considerations. $^1$H NMR (300 MHz) and $^{13}$C NMR (75 Hz) spectra of the ADMET polymers and monomers were recorded in $CDCl_3$ or $C_6D_6$ on either a Mercury series or Varian VXR-300 NMR super-conducting spectrometer. Chemical shifts were referenced to residual $CHCl_3$ (7.25 for $^1$H and 77.23 for $^{13}$C). High-resolution mass spectroscopy was performed at the University of Florida facility. Elemental analysis was carried out by Atlantic Microlab Inc. (Norcross, Ga.).

Gel permeation chromatography (GPC) of the unsaturated ADMET polymer was performed using two 300 mm Polymer Laboratories gel 5 μm mixed-C columns. The instrument consisted of a Rainin SD-300 pump, Hewlett-Packard 1047-A RI detector (254 nm), TC-45 Eppendorf column heater set to 35° C., and Waters U6K injector. The solvent used was THF, at a flow rate of 1.0 mL/min. Polymer samples were dissolved in HPLC grade THF (approximately 0.1% w/v) and filtered before injection. Retention times were calibrated to polystyrene standards from Polymer Laboratories (Amherst, Mass.).

Differential scanning calorimetry (DSC) was performed using a Perkin-Elmer DSC 7 at a heating rate of 10° C./min. Thermal calibrations were made using indium and freshly distilled n-octane as references for thermal transitions. Heats of fusion were referenced against indium. The samples were scanned for multiple cycles to remove recrystallization differences between samples and the results reported are the second scan cycle. Reported values are given as $T_m$ (melting peak).

Mechanical tests were performed at the University of Florida facility using an Instron model 1122 load frame upgraded with an MTS ReNew system running MTS TestWorks 4 software and a 500 g load cell for the experiments.

Materials. 5-bromo-1-pentene was purchased from Aldrich and stored over activated 4 Å molecular sieves. 11-bromo-undec-1-ene was purchased from Aldrich and distilled over $CaH_2$. Magnesium turnings (Aldrich) were activated by vacuum drying at 10° C. All reagent grade solvents were freshly distilled over a Na/K alloy, except for THF which was dried using K-benzophenone ketyl. Triethylene glycol (Aldrich) was dried by azeotropic distillation using toluene. Bis(trimethoxysilyl)ethane (Gelest) was dried over $CaH_2$ for 12 h under Ar, and distilled before use. All other compounds were used as received. Any necessary chlorosilanes were purchased from Gelest and used as received. Deuterated solvents (Cambridge Isotope Laboratories) were stored over activated 4 Å sieves. The metathesis catalysts $Cl_2Ru(IMes)(PCy_3)[=CHPh]$ (Grubbs' $2^{nd}$ generation) and $[Mo=CHCMe_2Ph(=N—C_6H_3-i-Pr_2-2,6)(OCMe(CF_3)_2)_2]$ (Schrock's) were synthesized according to literature procedure. Scholl, M.; Trnka, T. M.; Morgan, J. P.; Grubbs, R. H. *Tetrahedron Lett.* 1999, 1, 953; Schrock, R. R.; Murdzek, J. S.; Bazan, G. C.; Robbins, J.; DiMare, M.; O'regan, M. *J. Am. Chem. Soc.* 1990, 112, 3875; Bazan, G. C.; Oskam, J. H.; Cho, H.-N.; Park, L. Y.; Schrock, R. R. *J. Am. Chem. Soc.* 1991, 113, 6899.

Monomer synthesis. Monomer 1 and 2 (FIG. 1) were synthesized as described in Brzezinska, K. R.; Schitter, R.; Wagener, K. B. *J. Polm. Sci.; Part A; Polymer Chemistry*, 2000, 38, 1544.

Tris(4-pentenyl)methylsilane (6) (FIGS. 2, 3). A 250 mL three-necked round bottom flask equipped with an additional funnel, condenser, and stir bar was flame-dried under vacuum, and then flushed with argon. Magnesium turnings (2.1 g, 0.087 mol) and dry diethyl ether (50 mL) were added. A solution of 5-bromo-1-pentene (11.8 g, 0.08 mol) and 50 mL of diethyl ether was added drop wise to maintain constant reflux. After addition, the mixture was refluxed for an additional hour, followed by cooling to room temperature. Upon cooling, a mixture of trichloromethylsilane (3.32 g, 0.022 mol) in $Et_2O$ (10 mL) was added slowly followed by refluxing for 2 hours. The solution was cooled and the product was diluted with 50 mL of dry pentane and filtered via filter cannulation. The combined organics were evaporated under reduced pressure, yielding 6.5 g of a clear, colorless liquid.

The crude product was purified by column chromatography using straight hexanes. Monomer 6 was collected in 80% and the following spectral properties were observed: $^1$H NMR (CDCl$_3$): δ(ppm) −0.05 (s, 3H), 0.5 (m, br, 6H), 1.4 (m, br, 6H), 2.05 (m, br, 6H), 5.0 (m, br, 6H), 5.8 (m, br, 3H), $^{13}$C NMR (CDCl$_3$): δ(ppm) −5.25, 13.36, 23.40, 37.79, 114.43, 138.99. EI/HRMS: [M-C$_5$H$_9$]$^+$ calcd. for C$_{11}$H$_{21}$Si: 181.1412, found: 181.1412; Elemental analysis Calcd. for C$_{16}$H$_{30}$Si: 76.72 C, 12.07 H. found: 76.69 C, 12.18 H.

Diundecenyltriethylane glycol (9) (FIG. 3). The synthetic procedure was modified from published procedures. See, Chen, Y.; Baker, G. L. *J. Org. Chem.* 1999, 64, 6870. Sodium hydride (6.5 g, 0.27 mol, 60% dispertion) was placed in a flame-dried, Ar-purged, three-necked 1000 mL round-bottom flask equipped with a stir bar, condenser, and an additional funnel. Dried triethylene glycol (8 g, 0.068 mol) and 260 mL of dry THF were combined in a flame-dried 500 mL Schlenk flask. The solution was transferred to the additional funnel and the mixture was added drop wise under constant stirring. After 24 h, 11-bromoundecyl-1-ene (40 g, 0.17 mol) in 240 mL of THF was added and stirred for an additional 72 h at reflux. Upon cooling, 50 mL of water was added, stirred for 15 minutes, and extracted using ether. The combined organic extracts were washed with a saturated NaCl solution, dried over MgSO$_4$, filtered, and evaporated under reduced pressure. The crude product was then purified by column chromatography using hexanes/diethyl ether (80%:20%) as an eluent. The fractions were concentrated yielding 24 g of monomer 9. The following spectral properties were observed: $^1$H NMR (CDCl$_3$): δ(ppm) 1.25 (m, br, 24H), 1.60 (m, br, 4H), 2.10 (m, br, 4H), 3.53 (m, br, 4H), 3.60 (m, br, 12H), 4.95 (m, br, 4H), 5.85 (m, br, 2H); $^{13}$C NMR (CDCl$_3$): δ(ppm) 26.10, 28.94, 29.14, 29.45, 29.49, 29.51, 29.55, 29.62, 29.66, 33.81, 70.04, 70.64, 71.53, 114.06, 139.18. EI/HRMS: [M]$^+$ calcd. for C$_{28}$H$_{55}$O$_4$: 454.4022, found: 455.4121, Elemental analysis Calcd. for C$_{28}$H$_{55}$O$_4$: 73.96 C, 11.97 H. found: 73.91 C, 12.18 H.

General metathesis conditions. All monomers used in polymerization were purified and degassed prior to polymerization. All glassware was thoroughly cleaned and dried under vacuum before use. The polymerizations were initiated in an argon-filled glove box by placing the appropriate amount of monomer followed by either metathesis catalyst. In all cases the monomer:catalyst ratios were 250:1. The polymerizations were carried out in a schlenk reaction tube equipped with a Teflon stir bar. The flask was charged with the monomer, catalyst and slowly stirred for 2 minutes. The reaction tube was sealed using a Kontes Teflon valve and placed on a high vacuum line (<0.01 mm Hg). Initially, an intermediate vacuum was applied until the mixture became viscous. The reaction flask was then placed in a 40° C. oil bath and high vacuum. The temperature was gradually raised to 70° C. and the reaction was left for 72 h. After that time the reaction was stopped and the polymer was dissolved in toluene and precipitated in acetone.

Polymerization of diundecenyltriethylane glycol (9) (FIG. 3). The monomer was polymerized using the above procedure. Monomer 9 (0.5 g, 0.0021 mol) was added to Grubbs' 2$^{nd}$ generation catalyst (7.3 mg, 8.58×10$^{-6}$ mmol). The following properties were observed: $^1$H NMR (CDCl$_3$): δ(ppm) 1.25 (m, br, 24H), 1.60 (m, br, 4H), 2.10 (m, br, 4H), 3.53 (m, br, 4H), 3.60 (m, br, 12H), 5.56 (br, 2H); $^{13}$C NMR (CDCl$_3$): δ(ppm) 25.91, 26.06, 27.17, 28.96, 29.10, 29.16, 29.31, 29.43, 29.46, 29.60, 29.73, 32.49, 32.57, 70.01, 70.57, 70.58, 71.50, 130.30. GPC data (THF vs. polystyrene standards): $M_n$=27 770; P.D.I. ($M_w/M_n$)=1.55. DSC Results: Tm (peak) =35.7° C., Δh=86.8 J/g; Recrystallization T$_{recl.}$=20.1° C., Δh=−88.8 J/g Tripolymerization of monomers 1, 2, and 6 (FIG. 2). To produce copolymer 7, a mixture of monomers 1, 2 and 6 were prepared in a dry-box under an Ar atmosphere. Copolymer 7 was prepared using 1:20:1 monomer ratios: monomer 1 (0.17 g, 5.0×10$^{-4}$ mol), monomer 2 (3 g 0.01 mol) and monomer 6 (0.13 g, 5.2×10$^{-4}$ mol). The monomers were stirred for 5 minutes to ensure a homogenous mixture before the addition of either 2$^{nd}$ generation Grubbs' catalyst (0.037 g, 4.41×10$^{-5}$ mol), or Schrock's catalyst (0.034 g, 4.41×10$^{-4}$ mol). The reaction mixture was stirred under vacuum for 10 minutes. The polymerization mixture was then poured out on a Teflon® plate and placed in a vacuum oven at 70° C. for 72 h. Rigorous bubbling of the ethylene gas was observed, followed by formation of a thin film. After 72 h the Teflon® plate was removed from a vacuum oven and exposed to the atmospheric moisture. If Schrock's catalyst is used, the reaction mixture can be poured out onto the Teflon® plate in a glove box. The Teflon® plate is placed in a vacuum dessicator, removed from the glove box, and placed on a high vacuum line at room temperature for 72 h. After that time the thin film was exposed to atmospheric moisture.

Tripolymerization of monomers 1, 9, and 6 (FIG. 3). The monomers were prepared as described above. Copolymer 10 was prepared by mixing monomer 1 (0.11 g, 3.3×10$^{-4}$ mol), monomer 9 (3 g, 6.6×10$^{-3}$ mol), and monomer 6 (0.086 g, 3.46×10$^{-4}$ mol) resulting in 1:20:1 monomer ratios. Following the procedure described for copolymer 7, all monomers were mixed and stirred prior to the addition of the catalyst. In this case, 2$^{nd}$ generation Grubbs' catalyst (0.035 g, 4.1×10$^{-5}$ mol) was used. The reaction mixture was stirred, sealed, removed from the glove box, and placed for 5-10 minutes on a high vacuum line. After that the reaction mixture was transferred to the Teflon® plate and placed in a vacuum oven at 70° C. After 72 h, the Teflon® plate was removed and the thin film was exposed to the atmospheric moisture.

Example 2

Results

Based on the amount of either comonomer, polymers that exhibited a rigid or an elastic nature were synthesized. The "latent reactive" methoxy bonds were not metathesis labile and did not interfere with the polymerization mechanism. The initial silicon thermoset copolymers were produced as freestanding films that exhibited low tensile strength. See Table 1 below.

The reactions described above employ "soft" and "hard" monomers as reactants. The soft monomer is a carbosiloxane monomer that contains a siloxane bond (Si—O—Si) which promotes flexibility and mobility. The hard monomer is a carbosilane monomer that when cross-linked inhibits flexibility and mobility. Depending on the ratio of monomers polymerized, the methods described herein allow production of a wide range of copolymers including those exhibiting high elasticity (e.g., having a high percentage of siloxane) or high rigidity (e.g., having a low percentage of siloxane). Referring to reaction depicted in FIG. 1, the initial cross-linking sites are placed on the hard segment exclusively. This placement is important as placing such sites in the soft segment results in the formation of a brittle material.

An ADMET copolymer containing approximately 10% hard comonomer displays good elastic behavior. Chain-end cross-linking using tripentenylmethylsilane (monomer 6). Monomer 6 was synthesized by simple Grignard reaction of 5-bromo-1-pentene with trichloromethylsilane, which after workup produced an analytically pure trifunctional monomer. Monomer 6 was combined with monomers 1 and 2 (FIG. 1) and subjected to ADMET as illustrated in FIG. 2. The tripolymer was produced using the hard and soft system described above in combination with cross-linker 6 in a 1:20:1 ratio, respectively. Schrock's molybdenum catalyst at room temperature or $2^{nd}$ generation Grubbs' catalyst at a temperature of 67-70° C. under vacuum was used. After all the components were thoroughly mixed, the polymerizations were initiated using a 250:1 monomer:catalyst ratio regardless of catalyst used. Upon initiation, the reaction mixture was poured out on a Teflon® plate and placed either in a vacuum desiccator for Schrock's catalyst, or in a vacuum oven for the second-generation Grubbs' catalyst. In both cases, solvent-resistant elastic thermosets were produced. The solvent resistance was a result of the slight cross-linking produced, using the trifunctional monomer 6. The free-standing film was then exposed to atmospheric moisture to activate the "latent cross-links".

The effect of increasing the length of a selected phase on the elasticity of the polymer was investigated. Monomer 9 was first homopolymerized with standard bulk polycondensation ADMET conditions in order to check its compatibility with the catalyst systems. Only a second-generation Grubbs' catalyst was able to produce a linear polymer having an $M_n=27\ 770$ and PDI=1.55 after workup. In the case of Schrock's molybdenum catalyst, decomposition most likely occurred due to the catalyst's inability to tolerate oxyphilic or Lewis basic substrates. Thermal analysis performed on a homopolymer resulted in melting temperature at 35.7° C. and a recrystallization temperature at 16.6° C. revealing its semi-crystalline properties. After repeated scanning, both the enthalpy of melting and the enthalpy of recrystallization exhibit the same energy.

After checking its compatibility with the ADMET polymerization catalyst, the carbosiloxane soft monomer 2 was replaced with monomer 9 (FIG. 3). The same 1:20:1 monomer ratio along with the same catalyst loading (250:1) was employed. The resulting polymer exhibited enhanced elastic properties relative to the chemistry depicted in FIG. 2, even before latent cross-linking in the hard segment was induced. Its tensile strength is included in Table 1 for comparison to previously made ADMET materials, as well as, a commercially available silicon elastomer.

Referring to Table 1, thin film 4, composed only from monomer 2 and 1 exhibited a modulus of 0.16 MPa and 20% elongation. Film 8, made by increasing cross-link density using a chain-end cross-linker 5, exhibited enhanced mechanical properties (data not shown). A significant change in a modulus (6 MPa) and in elongation (500%) was observed for a film 11, the tripolymer composed from the soft phase containing polyoxyethylene (monomer 9), and monomer 1 (hard), and a chain-end cross-linker 5.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A polymer comprising at least two cross-linkable polymers selected from the group consisting of the polymer of Formula I, the polymer of Formula II, and combinations thereof, wherein the at least two cross-linkable polymers are cross-linked via a chain-end crosslink, a Si—O—Si linkage, or both, and wherein Formula I is a polymer comprising the structure:

wherein:
R is a latent reactive group selected from the group consisting of hydrogen, alkoxy, phenoxy, and halogen,
R' is selected from the group consisting of alkyl, phenyl, hydrogen, halogen, alkoxy, and phenoxy,
$R_1$ is a hydrocarbon chain having at least two $CH_2$ groups,
coefficients z, x' and y' are integers greater than or equal to 1,
coefficient y is an integer greater than or equal to 2, and
C is a chain-end cross-linking molecule derived from a compound selected from:

TABLE 1

Mechanical properties of the unsaturated ADMET copolymers and a commercially available elastomer

| Materials | Modulus (MPa) | Tensile Strength (MPa) | Elongation (%) |
|---|---|---|---|
| Film 4 | 0.16 | 0.2 | 20 |
| Film 11 | 6 | 0.6 | 500 |
| "Gelest Zipcone f Series" filler-free fast-cure pure silicone elastomers | 2 | 0.7 | 150 |

-continued wherein:
x is an integer greater than or equal to 2,
R" is any hydrocarbon,
X is OMe, OR" or NR", and
coefficient a is an integer ranging from 0 to 3; and
Formula II is a polymer comprising the structure:

wherein, coefficients x, y and z are integers greater than or equal to 1, and R" is selected $(CH_2)_nCH=CH_2$ and $(CH_2)_nCH=$, wherein, $(CH_2)_nCH=$ is a branching site whereby adjacent polymers are cross-linked and n is an integer greater than or equal to 2.

2. The polymer of claim 1, wherein the Formula I chain-end cross-linking molecule (C) is derived from a compound selected from the group consisting of compound 5 and compound 6 having the structure:

5

6 wherein, x is an integer greater than or equal to 2.

* * * * *

UNITED STATES PATENT AND TRADEMARK OFFICE
CERTIFICATE OF CORRECTION

PATENT NO.       : 7,754,842 B2
APPLICATION NO.  : 12/176831
DATED            : July 13, 2010
INVENTOR(S)      : Kenneth B. Wagener et al.

It is certified that error appears in the above-identified patent and that said Letters Patent is hereby corrected as shown below:

Column 1,
Line 15, "This invention was made with U.S. government support under grant number DAAD19-00-1-0160 awarded by the Army Research Office. The U.S. government may have has certain rights in the invention." should read --This invention was made with U.S. government support under grant number DAAD19-00-1-0160 awarded by the Army Research Office. The U.S. government has certain rights in the invention.--

Signed and Sealed this

Twelfth Day of October, 2010

David J. Kappos
*Director of the United States Patent and Trademark Office*

UNITED STATES PATENT AND TRADEMARK OFFICE
CERTIFICATE OF CORRECTION

PATENT NO.        : 7,754,842 B2
APPLICATION NO. : 12/176831
DATED             : July 13, 2010
INVENTOR(S)       : Kenneth B. Wagener et al.

It is certified that error appears in the above-identified patent and that said Letters Patent is hereby corrected as shown below:

Column 5,
Line 55, "(2, J, 4, 5, or more)" should read --(2, 3, 4, 5, or more)--.

Column 8,
Line 30, "drying at 10° C." should read --drying at 100°C.--.
Line 51, "J. Polm. Sci.;" should read --J. Polym. Sci.;--.

Column 9,
Line 61, "mmol)." should read --mol).--

Signed and Sealed this

Twenty-first Day of December, 2010

David J. Kappos
*Director of the United States Patent and Trademark Office*